(12) United States Patent
Old

(10) Patent No.: US 7,985,765 B2
(45) Date of Patent: Jul. 26, 2011

(54) THERAPEUTIC SUBSTITUTED PYRROLES

(75) Inventor: David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/542,366

(22) Filed: Aug. 17, 2009

(65) Prior Publication Data

US 2010/0048664 A1 Feb. 25, 2010

Related U.S. Application Data

(60) Provisional application No. 61/090,336, filed on Aug. 20, 2008.

(51) Int. Cl.
| | |
|---|---|
| *A61K 31/4025* | (2006.01) |
| *C07D 403/06* | (2006.01) |
| *C07D 403/12* | (2006.01) |
| *C07D 405/06* | (2006.01) |
| *C07D 405/12* | (2006.01) |
| *C07D 409/06* | (2006.01) |
| *C07D 409/12* | (2006.01) |

(52) U.S. Cl. ......... 514/422; 548/518; 548/527; 548/517
(58) Field of Classification Search .................. None
See application file for complete search history.

(56) References Cited

U.S. PATENT DOCUMENTS

| | | |
|---|---|---|
| 6,437,146 B1 | 8/2002 | Hattori et al. |
| 6,573,294 B1 | 6/2003 | Old et al. |
| 6,710,072 B2 | 3/2004 | Burk et al. |
| 7,473,702 B2 | 1/2009 | Old et al. |
| 7,476,747 B2 | 1/2009 | Old et al. |
| 2003/0120079 A1 | 6/2003 | Elworthy et al. |
| 2007/0129552 A1 | 6/2007 | Donde |

FOREIGN PATENT DOCUMENTS

| | | |
|---|---|---|
| WO | WO94/13295 | 8/1994 |
| WO | WO95/19964 | 7/1995 |
| WO | WO03/103604 | 12/2003 |
| WO | WO2004/037813 | 5/2004 |
| WO | WO2008/024765 | 2/2008 |
| WO | WO 2010019905 A1 * | 2/2010 |

OTHER PUBLICATIONS

Saeed, et al. J. Chem. Res., Synop. 7:222 (1989).*
Francis A. Carey, Organic Chemistry, McGraw-Hill Book Company: New York, 1987, pp. 11-13.
Richard B. Silverman "Prodrugs and Drug Delivery Systems", Organic Chemistry of Drug Design and Drug Action, 2d Ed., Elsevier Academic Press: Amsterdam, 2004, pp. 496-557.
Kwon, Younggil, Handbook of Essential Pharmacokinetics, Pharmacodynamics and Drug Metabolism for Industrial Scientists . Jun. 24, 2001, Apr. 24, 2008.
Metabolomics [online], Retrieved from the Internet Apr. 24, 2008, www.en.wikipedia.org/wiki/Metabolomics.
Stella, Valentino J, Expert Opinion of Therapeutic Patents, Prodrugs as therapeutics, 2004 14(3): 277-280.
Wolff et al. (Burger's Medicinal Chemistry, 5th Ed., vol. 1, pp. 975-977, 1994.

* cited by examiner

*Primary Examiner* — Yong Chu
*Assistant Examiner* — Michael Barker
(74) *Attorney, Agent, or Firm* — Kevin J. Forrestal; John E. Wurst

(57) ABSTRACT

Disclosed herein is a compound represented by a formula:

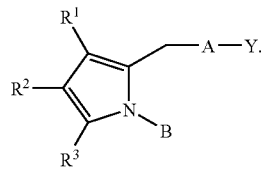

Therapeutic methods, compositions, and medicaments related thereto are also disclosed.

18 Claims, No Drawings

THERAPEUTIC SUBSTITUTED PYRROLES

RELATED APPLICATION

This application claims the benefit of U.S. Provisional Application Ser. No. 61/090,336, filed Aug. 20, 2008, the disclosure of which is hereby incorporated in its entirety herein by reference.

DESCRIPTION OF THE INVENTION

Disclosed herein is a compound represented by a formula:

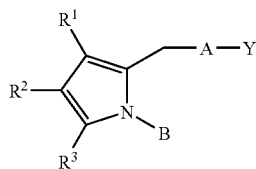

wherein Y is $C_{0-14}H_{1-30}O_{1-4}S_{0-2}N_{0-4}P_{0-1}$ and is: an organic acid functional group, or an amide or ester thereof; hydroxymethyl or an ether thereof; or a tetrazolyl functional group;

A is —$(CH_2)_5$—, —$CH{=}CH(CH_2)_3$—, or —$C{\equiv}C(CH_2)_3$—, wherein:
  a) 1 or 2 —$CH_2$— may be replaced with —O— or —S—, or
  b) —$CH_2CH_2$—, —$(CH_2)_3$—, or —$(CH_2)_4$— is replaced by —Ar— and 1 —$CH_2$— may be replaced by —O— or —S—, Ar is aryl of a formula $C_{3-10}H_{0-23}N_{0-4}O_{0-4}S_{0-4}F_{0-5}Cl_{0-3}Br_{0-3}I_{0-3}$, Ar is aryl of a formula $C_{3-10}H_{0-23}N_{0-4}O_{0-4}S_{0-4}F_{0-5}Cl_{0-3}Br_{0-3}I_{0-3}$, $R^1$, $R^2$, and $R^3$ are independently —H, —F, —Cl, —Br, —I, or a moiety of a formula $C_{0-6}H_{0-14}N_{0-1}O_{0-2}S_{0-1}$.

B is aryl of a formula $C_{5-20}H_{0-45}N_{0-4}O_{0-4}S_{0-4}F_{0-5}Cl_{0-3}Br_{0-3}I_{0-3}$.

These compounds are useful for reducing intraocular pressure, treating glaucoma or intraocular pressure, growing hair, or improving the appearance of hair in mammals, including human beings. Growing hair includes increasing the length or radius of individual hairs as well as increasing the number of hairs present in a given area. Improving the appearance of hair includes improving the color, such as darkening, or improving its gloss, shine, or other properties related to the reflection, absorption, emission, or dispersion of light.

Unless otherwise indicated, reference to a compound should be construed broadly to include the compound and pharmaceutically acceptable salts, prodrugs, tautomers, alternate solid forms, non-covalent complexes, and combinations thereof, of a chemical entity of a depicted structure or chemical name.

Any description of a compound made herein is not intended to encompass compounds having structural features that violate the basic principles of chemistry such as containing an atom having too many or too few electrons in its valence shell (see Francis A. Carey, Organic Chemistry, McGraw-Hill Book Company: NewYork, 1987, pp. 11-13). It is also not intended to encompass compounds that are too reactive or otherwise too unstable to be useful as described herein. For example, it is not intended to encompass compounds that cannot either: 1) be put into a bottle with an excipient for subsequent use in treating a mammal as disclosed herein, or 2) be put into a bottle as a salt or a prodrug of the compound with an excipient for subsequent use in treating a mammal as disclosed herein.

Unless otherwise indicated, if a term is used to describe more than one structural feature of the compounds disclosed herein, it should be assumed that the term has the same meaning for all of those features. Similarly, a subgroup of that term applies to every structural feature described by that term.

Unless stereochemistry is explicitly and unambiguously depicted, a structure is intended to include every possible stereoisomer, both pure or in any possible mixture.

"Treat," "treating," or "treatment" refer to the use of a compound, composition, therapeutically active agent, or drug in the diagnosis, cure, mitigation, treatment, or prevention of disease or other undesirable condition.

A pharmaceutically acceptable salt is any salt of the parent compound that is suitable for administration to an animal or human, or any salt which may form in vivo as a result of administration of an acid, another salt, or a prodrug which is converted into an acid or salt. A salt comprises one or more ionic forms of the compound, such as a conjugate acid or base, associated with one or more corresponding counterions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —$CO_2(CH_2)_2OH$,

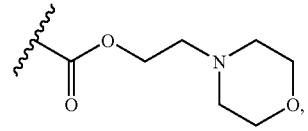

and the like.

Tautomers are isomers that are in rapid equilibrium with one another. For example, tautomers may be related by transfer of a proton, hydrogen atom, or hydride ion.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species. In these complexes, the compound and the additional chemical species have attractive interactions that are not covalent bonds. Examples include solvates, hydrates, charge transfer complexes, and the like.

An organic acid functional group is an acidic functional group on an organic molecule. For example, organic acid functional groups may comprise an oxide of carbon, sulfur, or phosphorous, such as a carboxylic acid, sulfonic acid, or phosphonic acid functional group.

An amide is a functional group where an —OH of an organic acid is replaced by a nitrogen atom which nitrogen atom is directly attached to: 1) two carbon atoms, 2) two hydrogen atoms, 3) a carbon atom and a hydrogen atom, or 4) a sulfur atom of a sulfonyl (—SO$_2$—) and hydrogen atom.

An ester is a functional group where an —OH of an organic acid is replaced by an oxygen atom which is directly attached to a carbon atom.

The structures below depict examples different organic acid functional groups and their associated amides and esters.

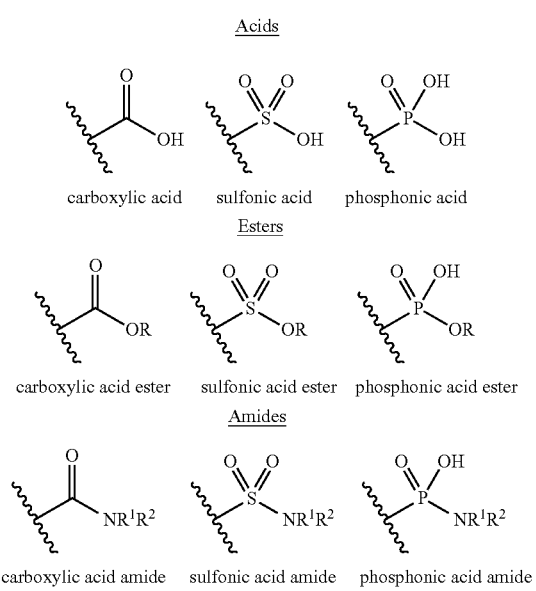

In these examples, R could be alkyl, another hydrocarbyl, or a species such as —CH$_2$CH$_2$OH. R$^1$ and R$^2$ could be hydrogen, alkyl, another hydrocarbyl, or alkyl sulfonyl (i.e. —SO$_2$-alkyl).

Hydrocarbyl is a moiety consisting only of hydrogen atoms and carbon atoms.

Examples include:
1. alkyl, which is hydrocarbyl that contains no double or triple bonds, such as:
   a. linear alkyl, e.g. methyl, ethyl, n-propyl, n-butyl, n-pentyl, n-hexyl, etc.,
   b. branched alkyl, e.g. iso-propyl, t-butyl and other branched butyl isomers, branched pentyl isomers, etc.,
   c. cycloalkyl, e.g. cyclopropyl, cyclobutyl, cyclopentyl, cyclohexyl, etc., and
   d. combinations of linear, branched, and/or cycloalkyl;

C$_{1-3}$ alkyl is alkyl having from 1 to 3 carbon atoms such as methyl, ethyl, propyl, isopropyl, cyclopropyl, etc.

C$_{1-6}$ alkyl is alkyl having from 1 to 6 carbon atoms such as methyl, ethyl, propyl isomers, butyl isomers, pentyl isomers, hexyl isomers, cyclopropyl, cyclobutyl, cyclopentyl, cyclohexyl, etc.

C$_{1-10}$ alkyl is alkyl having from 1 to 10 carbon atoms.

2. alkenyl, which is hydrocarbyl having 1 or more double bonds, including linear, branched, or cycloalkenyl;
3. alkynyl, which is hydrocarbyl having 1 or more triple bonds, including linear, branched, or cycloalkynyl;
4. unsubstituted phenyl, naphthyl, etc.; and
5. combinations of alkyl, alkenyl, akynyl; and unsubstituted phenyl, naphthyl, etc.

Hydroxyalkyl is alkyl-OH. For example, hydroxymethyl is —CH$_2$OH.

C$_{1-6}$ hydroxyalkyl is hydroxyalkyl having from 1 to 6 carbon atoms, such as hydroxymethyl, hydroxyethyl isomers, hydroxypropyl isomers, hydroxybutyl isomers, hydroxypentyl isomers, hydroxyhexyl isomers, etc.

C$_{1-10}$ hydroxyalkyl is hydroxyalkyl having from 1 to 10 carbon atoms.

An ether is a moiety comprising an oxygen attached to two different carbon atoms. For example, an ether of hydroxymethyl is —CH$_2$—O-hydrocarbyl. Another example is —O-alkyl.

C$_{1-3}$—O-alkyl is —O-alkyl having 1, 2, or 3 carbon atoms such as —O-methyl, —O-ethyl, —O—C$_3$H$_7$.

C$_{1-10}$—O-allkyl is —O-alkyl having from 1-10 carbon atoms.

C$_{1-3}$—S-alkyl is —S-alkyl having 1, 2, or 3 carbon atoms such as —S-methyl, —S-ethyl, —S—C$_3$H$_7$.

C$_{1-10}$—S-allkyl is —S-alkyl having from 1-10 carbon atoms.

Acyl is

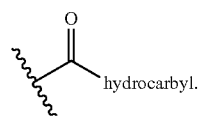

C$_{1-10}$ acyl is acyl having from 1-10 carbon atoms, such as formyl, acetyl, propionyl, butyryl, pentanoyl, hexanoyl, benzoyl, etc.

A tetrazolyl functional group has one of the tautomeric ring structures below:

The hydrogen on either tautomeric form may be replaced by a substituent as well. These moieties are also considered to be tetrazolyl functional groups.

Aryl is an unsubstituted or substituted aromatic ring or aromatic ring system. The ring or ring system atoms could all be carbon. Alternatively, heteroaryl, a subgenus of aryl, has one or more oxygen, sulfur, or nitrogen atoms in the ring or ring system.

Monocyclic aryl is aryl having only one ring.

Unsubstituted aryl refers to aryl with no substituents. Substituted aryl refers to aryl with one or more substituents. If a group is indicated as "aryl" the bond or bonds to that group directly attach to a carbon atom of an aromatic ring, and not to a substituent.

Any group may be a substituent subject to any restrictions placed upon the moiety that the aryl group is a part of. Examples of substituents include:

hydrocarbyl, as described above alkyl-CN, such as —CH$_2$—CN, —(CH$_2$)$_2$—CN; —(CH$_2$)$_3$—CN, and the like;

Hydroxy, —OH hydroxyalkyl, i.e. alkyl-OH, such as hydroxymethyl, hydroxyethyl, and the like;

polyhydroxyalkyl, i.e. alkyl having more than 1 —OH substituent;

ether substituents, including —O-alkyl, alkyl-O-alkyl, and the like;

thioether substituents, including —S-alkyl, alkyl-S-alkyl, and the like;

amine substituents, including —NH$_2$, —NH-alkyl, —N-alkyl$^1$alkyl$^2$ (i.e., alkyl$^1$ and alkyl$^2$ are the same or different, and both are attached to N), alkyl-NH$_2$, alkyl-NH-alkyl, alkyl-N-alkyl$^1$alkyl$^2$, and the like;

aminoalkyl, meaning alkyl-amine, such as aminomethyl (—CH$_2$-amine), aminoethyl, and the like;

ester substituents, including —CO$_2$-alkyl, —CO$_2$-phenyl, etc.;

other carbonyl substituents, including aldehydes; ketones, such as acyl, including, acetyl, propionyl, and benzoyl substituents;

fluorocarbons or hydroflourocarbons such as —CF$_3$, —CH$_2$CF$_3$, etc.; and other nitrogen containing substituents such as —CN and —NO$_2$, other sulfur containing subsitutents such as sulfide, sulfonyl or sulfoxide;

aryl;

combinations of the above are also possible, subject to the constraints defined;

Alternatively, a substituent may be —F, —Cl, —Br, or —I.

The terms imidazolyl, pyrrolyl, furanyl, oxazolyl, thiazolyl, thienyl, pyridinyl, and phenyl refer to both the unsubstituted and substituted versions of the monocyclic aryl rings below.

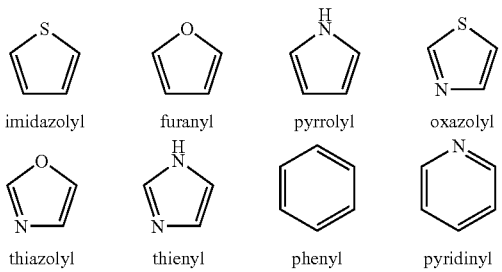

imidazolyl    furanyl    pyrrolyl    oxazolyl thiazolyl    thienyl    phenyl    pyridinyl Y is $C_{0-14}H_{1-30}O_{1-4}S_{0-2}N_{0-4}P_{0-1}$ and is: an organic acid functional group, or an amide or ester thereof; hydroxymethyl or an ether thereof; or a tetrazolyl functional group.

In any given formula, a subscript containing a range of values such as 0-14, 1-30, etc. indicates the number of that particular atom or group with which it is associated. For example, $C_{0-14}H_{1-30}O_{1-4}S_{0-2}N_{0-4}P_{0-1}$ indicates 0-14 carbon atoms, 1-30 hydrogen atoms, 1-4 oxygen atoms, 0-2 sulfur atoms, 0-4 nitrogen atoms, and 0-1 phosphorous atoms. Similarly $C_{1-10}$ alkyl indicates alkyl characterized by having 1-10 carbon atoms, and

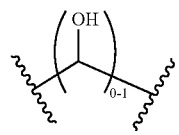

indicates that there are 0 or 1 hydroxymethylene groups (i.e. the group in parenthesis) present.

In one embodiment, Y is —CO$_2$R$^4$, —CONR$^5$R$^6$, —CON(CH$_2$CH$_2$OH)$_2$, —CONH(CH$_2$CH$_2$OH), —CH$_2$OH, —P(O)(OH)$_2$, —CONHSO$_2$R$^4$, —SO$_2$NR$^5$R$^6$,

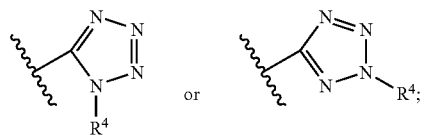

wherein R$^4$, R$^5$ and R$^6$ are independently H, $C_1$-$C_6$ alkyl, $C_{1-6}$ hydroxyalkyl, unsubstituted phenyl, or unsubstituted biphenyl.

In another embodiment, Y is —CO$_2$R$^4$.

In another embodiment, Y is —CO$_2$H, —CO$_2$CH$_3$, —CO$_2$CH$_2$CH$_3$, or —CO$_2$—C$_3$H$_7$.

In another embodiment Y is —CO$_2$(CH$_2$)$_2$OH or

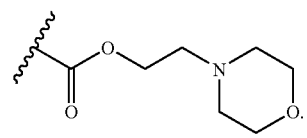

In another embodiment Y is —CONR$^5$R$^6$.

In another embodiment Y is —CO$_2$R$^5$, wherein R$^5$ is —H or $C_{1-6}$ alkyl.

In another embodiment Y is —CO$_2$R$^5$, wherein R$^5$ is —H or $C_{1-6}$ alkyl.

A is —(CH$_2$)$_5$—, —CH═CH(CH$_2$)$_3$—, or —C≡C(CH$_2$)$_3$—, wherein:

a) 1 or 2 —CH$_2$— may be replaced with —O— or —S—, or b) —CH$_2$CH$_2$—, —(CH$_2$)$_3$—, or —(CH$_2$)$_4$— is replaced by —Ar— and 1 —CH$_2$— may be replaced by —O— or —S—, Ar is aryl of a formula $C_{3-10}H_{0-23}N_{0-40}O_{0-4}S_{0-4}F_{0-5}Cl_{0-3}Br_{0-3}I_{0-3}$, Thus, A may be —(CH$_2$)$_5$—, —CH═CH(CH$_2$)$_3$—, or —C≡C(CH$_2$)$_3$—.

In the case that 1 or 2 —CH$_2$— moieties may be replaced with —O— or —S—, one or two sulfur or oxygen atoms takes the place of a methylene in the alkyl, alkenyl, or alkynyl chain. The structures depicted below are some typical examples of this.

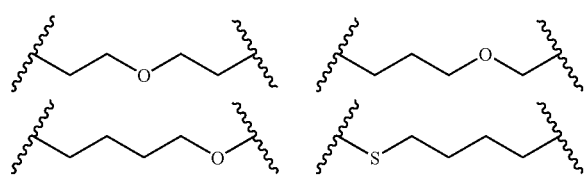

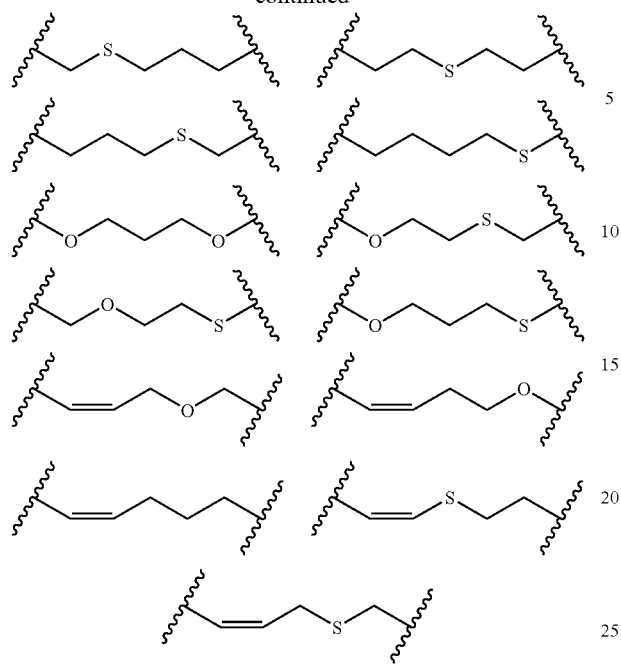
In the case that —CH$_2$CH$_2$—, —(CH$_2$)$_3$—, or —(CH$_2$)$_4$— is replaced by —Ar—, A may be a structure such as one of those shown below.
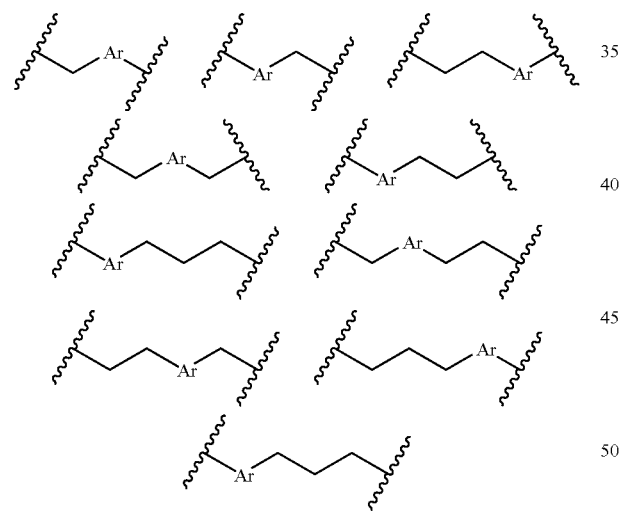
The statement that 1 —CH$_2$— may be replaced by —O— or —S— means that A may be a structure such as one of those shown below.
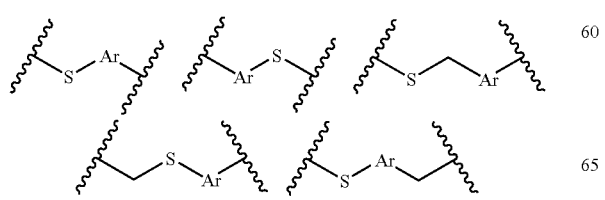
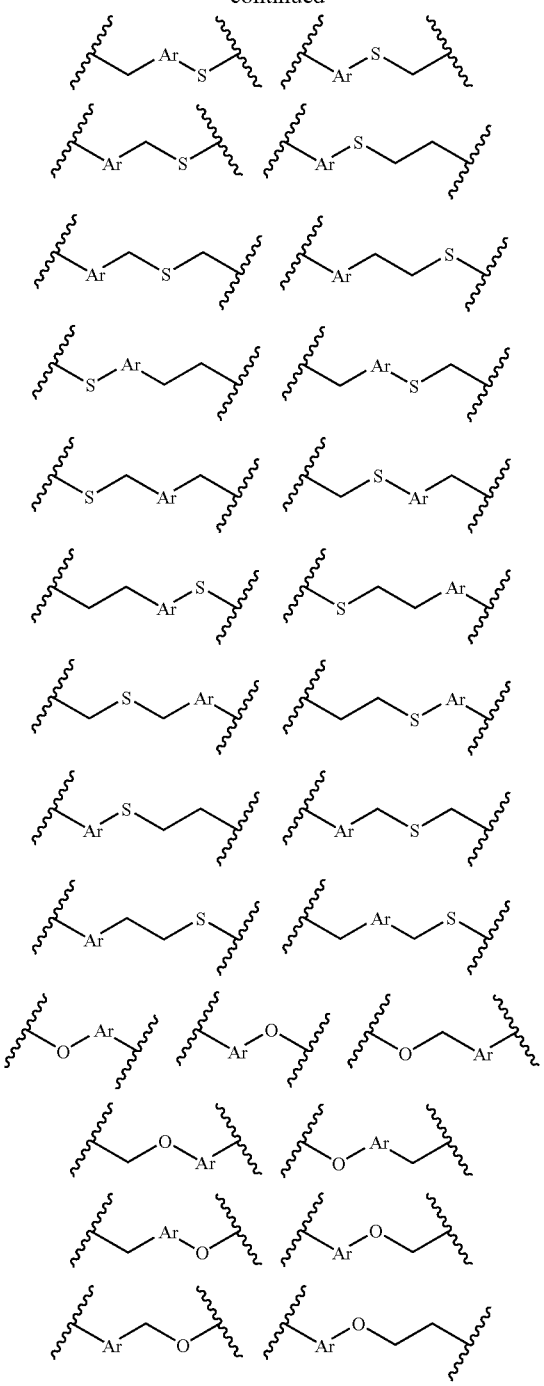
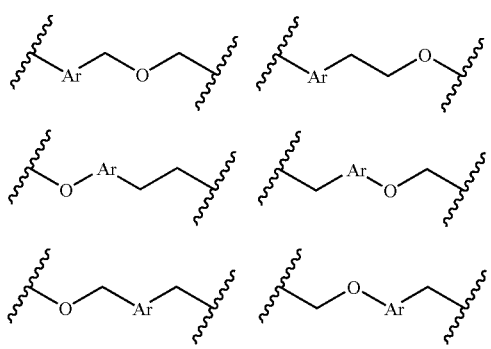

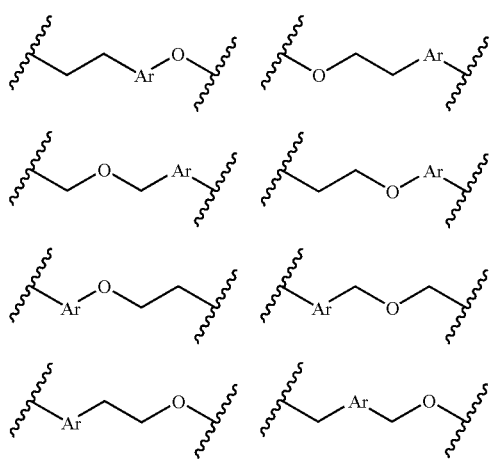

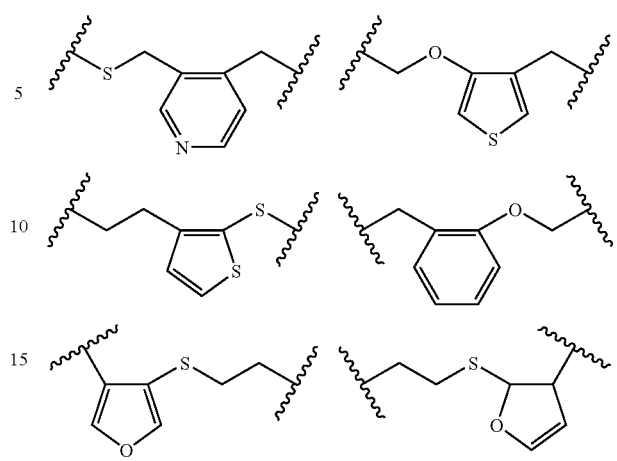

In one embodiment, A is —(CH$_2$)$_5$—, —CH═CH(CH$_2$)$_3$—, or —C≡C(CH$_2$)$_3$—, wherein:
a) 1 or 2 —CH$_2$— may be replaced with —O— or —S—, or
b) 1) a) —CH$_2$CH$_2$— is replaced by 1,2-attached —Ar—,
   b) —(CH$_2$)$_3$— is replaced by 1,3,-attached —Ar—, or
   c) —(CH$_2$)$_4$— is replaced by 1,4-attached —Ar—; and
2) 1 —CH$_2$— may be replaced by —O— or —S—, Examples of A Wherein —CH$_2$CH$_2$— is Replaced by 1,2-attached —Ar— and 1 —CH$_2$— Moiety May be Replaced by —O— or —S—

1,2-attached —Ar— indicates that the remainder of the A moiety attaches to —Ar— at two carbons that are adjacent on the ring. In the case of phenyl, this is the same as ortho substitution. For other aryls, 1,2-is the analogous substitution.

Thus, if —CH$_2$CH$_2$— is replaced by 1,2-attached —Ar—, structures such as those shown below are obtained.

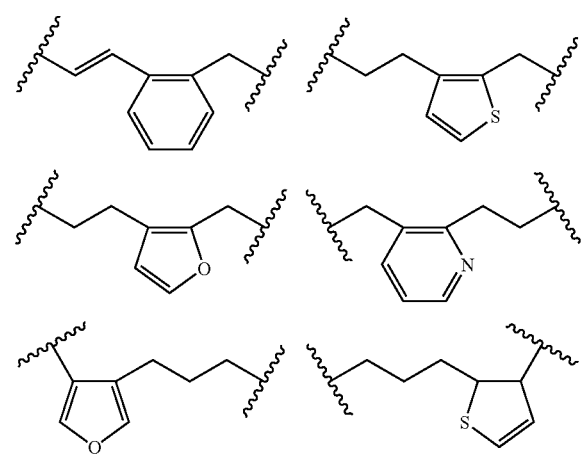

If 1 of the —CH$_2$— moieties is replaced with S or O, structures such as those shown below may be obtained.

Many other examples are possible by varying the type of aromatic ring, the position of an —O— or —S— (if present), and the position of the ring in the chain structure. Further variation is possible if substituents are present on the aromatic ring.

Examples of A Wherein —(CH$_2$)$_3$— is Replaced by 1,3-attached —Ar—, and 1 —CH$_2$— moiety may be Replaced by —O— or —S—

1,3-attached —Ar— indicates that the remainder of the A moiety attaches to carbon atoms on the aromatic ring which are separated by a single aromatic ring atom (e.g. ═CH—, —O—, —S—, —N—, etc.). In the case of phenyl, this is the same as meta substitution. For other aryls, 1,3- is the analogous substitution.

Thus, if —(CH$_2$)$_3$— is replaced by 1,3,-attached —Ar—, structures such as those shown below are obtained.

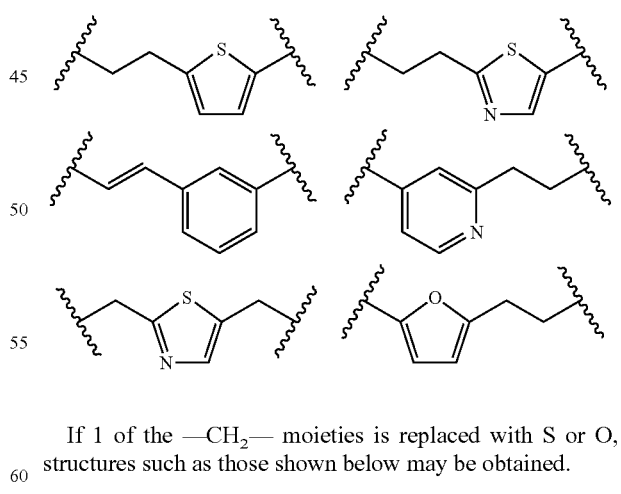

If 1 of the —CH$_2$— moieties is replaced with S or O, structures such as those shown below may be obtained.

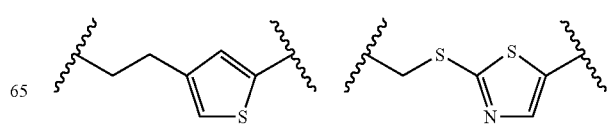

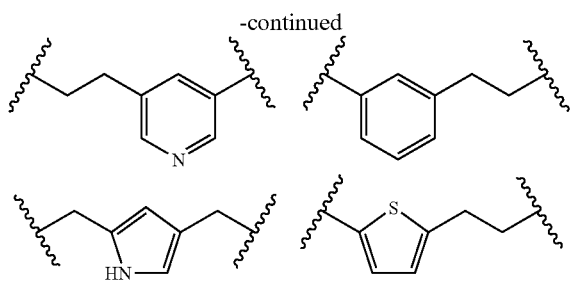

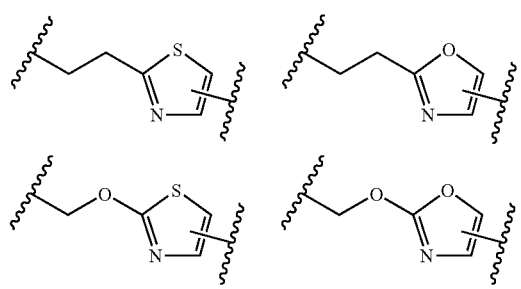

Many other examples are possible by varying the type of aromatic ring, the position of an —O— or —S— (if present), and the position of the ring in the chain structure. Further variation is possible if substituents are present on the aromatic ring.

Examples of A Wherein —(CH$_2$)$_4$— is Replaced by 1,3-attached —Ar—, and 1 —CH$_2$— Moiety May be Replaced by —O— or —S—

1,4-attached —Ar— indicates that the remainder of the A moiety attaches to carbon atoms on a six-membered aromatic ring (e.g. phenyl or pyridinyl) which are separated by two aromatic ring atoms (e.g. —CH=CH—, —O—CH=, =CH—S—, —C=N—, etc.). In the case of phenyl, this is the same as para substitution. For other aryls, 1,4- is the analogous substitution.

Thus, if —(CH$_2$)$_3$— is replaced by 1,3,-attached —Ar—, structures such as those shown below are obtained.

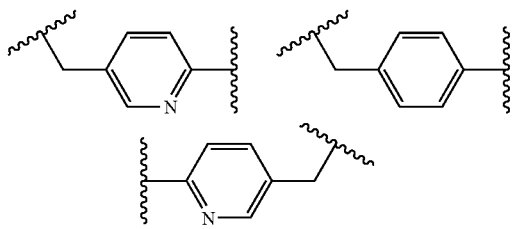

If 1 of the —CH$_2$— moieties is replaced with S or O, structures such as those shown below may be obtained.

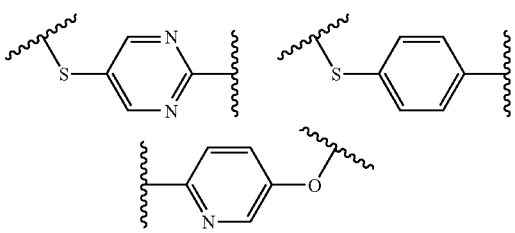

Many other examples are possible by varying the type of aromatic ring, the position of an —O— or —S— (if present), and the position of the ring in the chain structure. Further variation is possible if substituents are present on the aromatic ring.

In other embodiments, A has one of the following structures, wherein Y attaches to the ring.

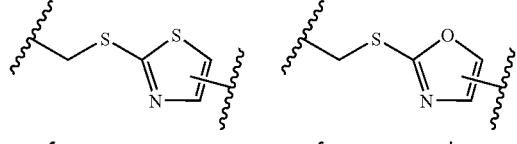

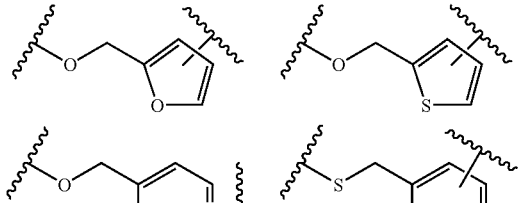

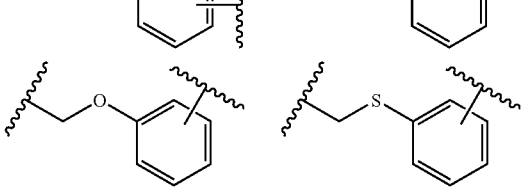

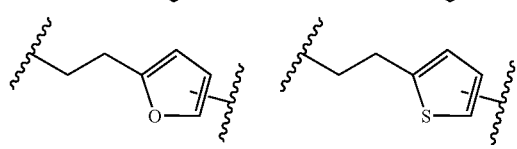

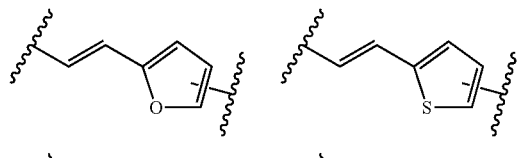

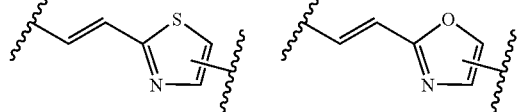

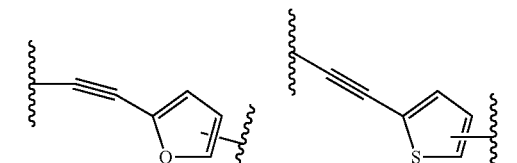

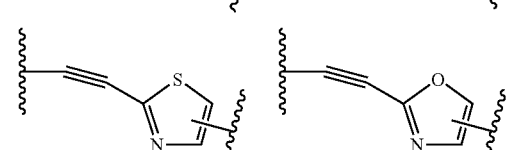

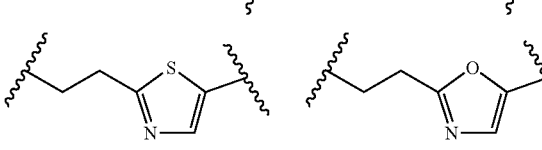

-continued

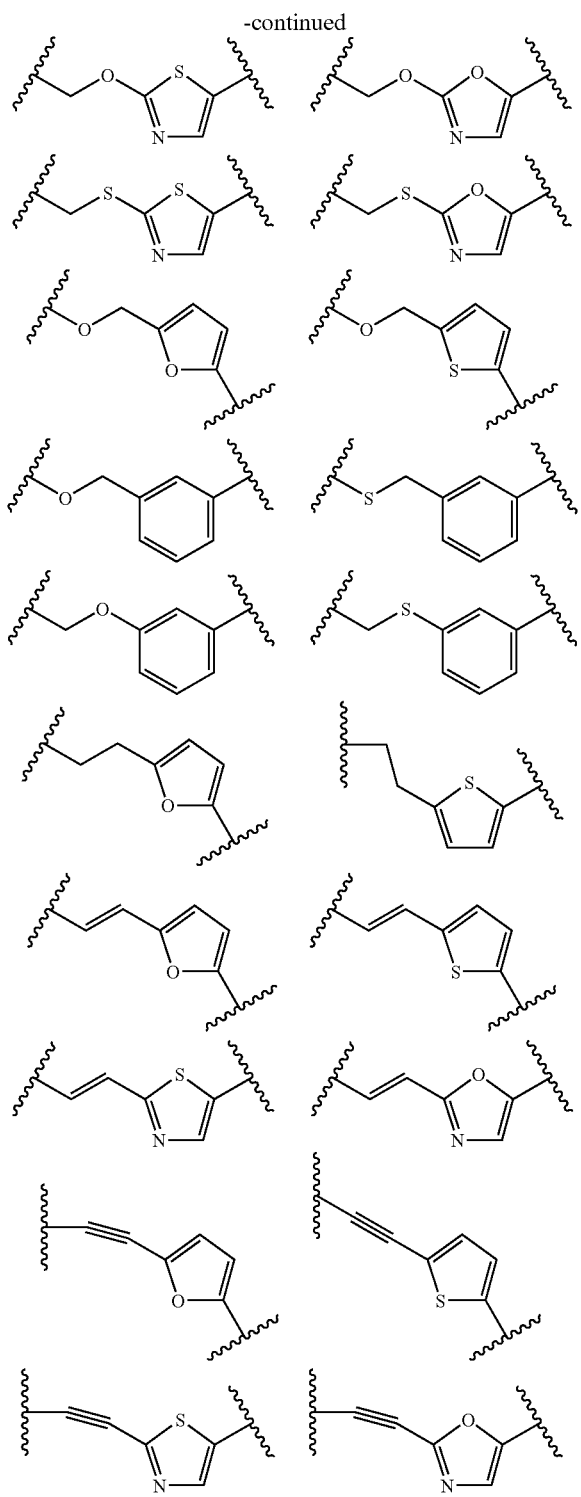

In one embodiment, A is —(CH$_2$)$_3$Ar—, wherein Ar is thienyl.

In one embodiment, A is —(CH$_2$)$_3$Ar—, wherein Ar is 1,3-attached thienyl.

In another embodiment, A is —(CH$_2$)$_2$ArCH$_2$, wherein Ar is thienyl.

In another embodiment, A is —(CH$_2$)$_2$ArCH$_2$, wherein Ar is 1,3-attached thienyl.

In another embodiment, A is —CH$_2$Ar(CH$_2$)$_2$, wherein Ar is thienyl.

In another embodiment, A is —CH$_2$Ar(CH$_2$)$_2$, wherein Ar is 1,3-attached thienyl.

In another embodiment, A is —(CH$_2$)$_2$Ar—, wherein Ar is thienyl with 1 or 2 substituents selected from F, Cl, Br, OH, and OCH$_3$, and 1 —CH$_2$— may be replaced by —O— or —S—.

Another embodiment is a compound represented by a formula:

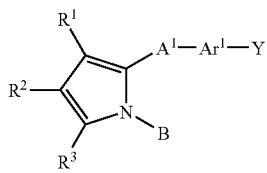

wherein A$^1$ is —(CH$_2$)$_3$—, —O(CH$_2$)$_2$—, —S(CH$_2$)$_2$—, —CH$_2$OCH$_2$—, —CH$_2$SCH$_2$—, —(CH$_2$)$_2$O—, or —(CH$_2$)$_2$S—;

Ar$^1$ is 1,3-attached thienyl, furyl, or pyrrolyl with 0, 1, or 2 substituents selected from, —F, —Cl, —Br, —CH$_3$, or —OCH$_3$.

R$^1$, R$^2$, and R$^3$ are independently —H, —F, —Cl, —Br, —I, or a moiety of a formula C$_{0-6}$H$_{0-14}$N$_{0-1}$O$_{0-2}$S$_{0-1}$.

Thus, compounds such as those examples shown below are possible.

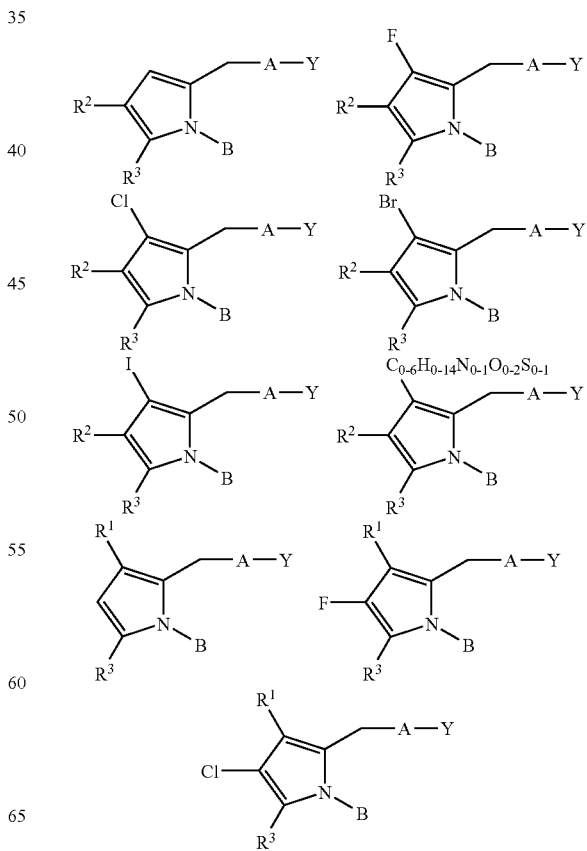

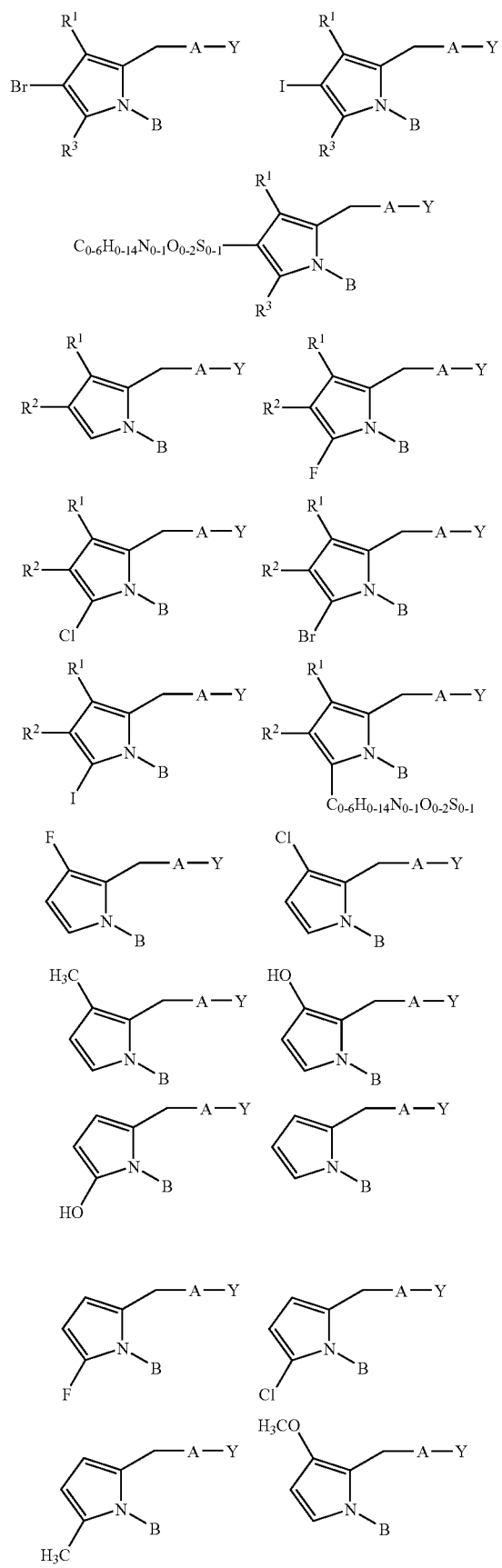
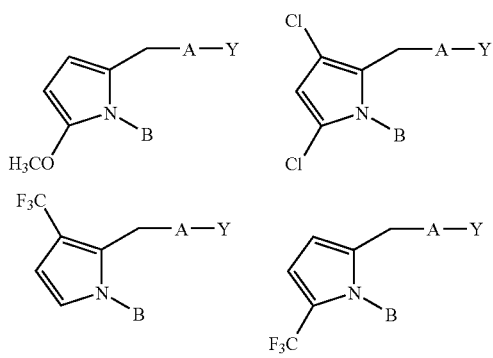

In one embodiment, $R^1$, $R^2$, and $R^3$ are acyclic, meaning that they contain no rings.

In another embodiment, $R^1$, $R^2$, and $R^3$ are independently selected from —F, —Cl, —Br, —I, —$CF_3$, —C(O)$CF_3$, —R, —C(O)R, $SO_2NR_2$, —OR, and —$NR_2$, wherein R is independently —H or $C_{1-6}$ alkyl.

B is aryl of a formula $C_{5-20}H_{0-45}N_{0-40}O_{0-4}S_{0-4}F_{0-5}Cl_{0-3}Br_{0-3}I_{0-3}$.

In another embodiment B is phenyl, pyridinyl, thienyl, or furyl, and B has 1, 2, or 3 substituents independently selected from —F, —Cl, —Br, —I, —$CF_3$, —C(O)$CF_3$, —$R^7$, —C(O)$R^7$, —$SO_2N(R^7)_2$, —$OR^7$, and —$N(R^7)_2$, wherein $R^7$ is $C_{1-10}$ alkyl with 0, 1, 2, or 3 —OH substituents, or $R^7$ is unsubstituted phenyl, pyridinyl, thienyl, or furyl.

Thus, compounds such as those below are contemplated.

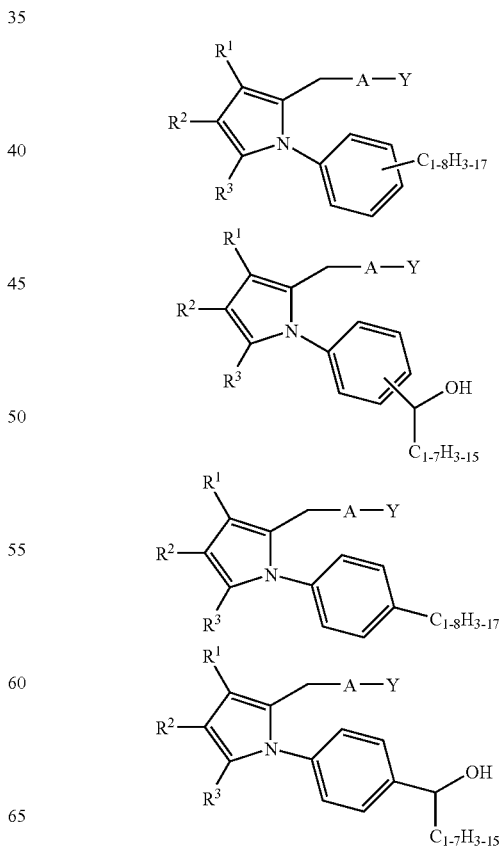

-continued

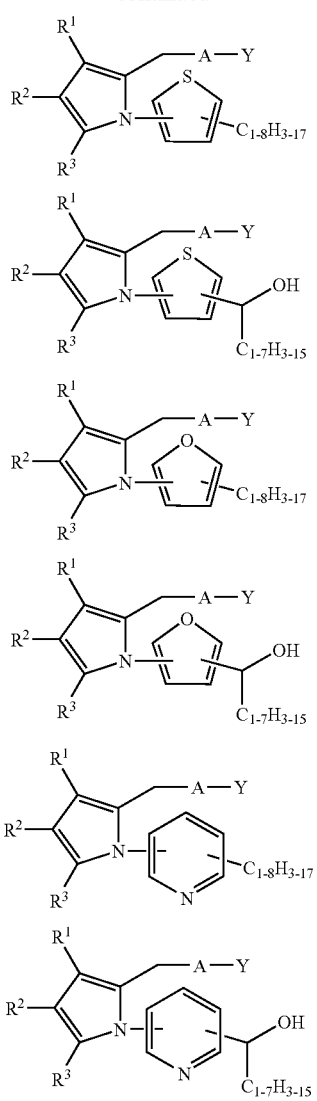

In another embodiment, B is phenyl with 1 substituent represented by:

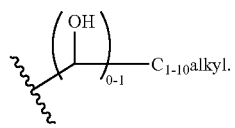

Another embodiment is a compound represented by a formula:

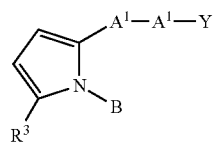

wherein $R^3$ is —H, —F, —Cl, or —Br.

Another embodiment is a compound represented by a formula:

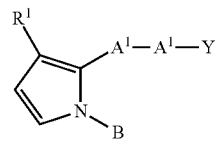

wherein $R^1$ is —H, —F, —Cl, or —Br.

In another embodiment, B is phenyl with 1 substituent having a formula $C_{2-10}H_{5-21}O_{0-2}$ which is alkyl, alkyl with 1 or two hydroxyl substituents, an ether, or a hydroxyether.

A hydroxyether is an ether with a hydroxyl substituent.

Another embodiment is a compound represented by a formula:

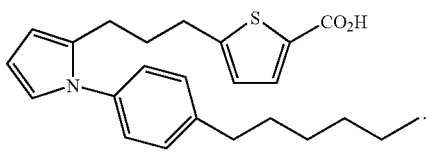

Another embodiment is a compound represented by a formula:

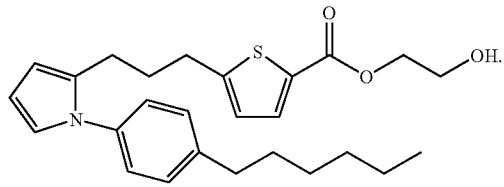

Other examples of useful compounds include:

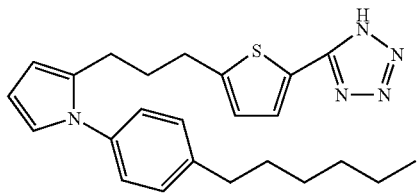

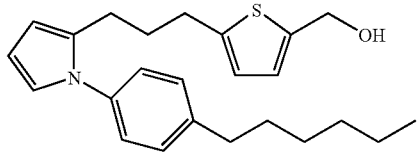

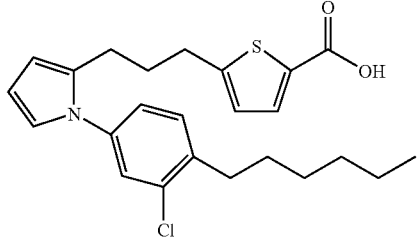

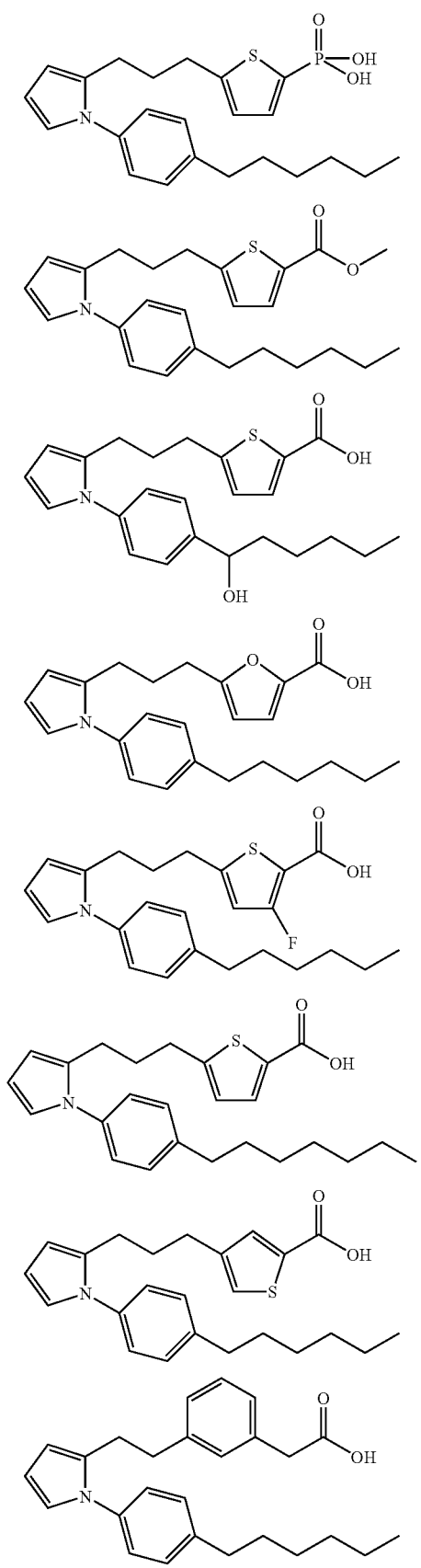
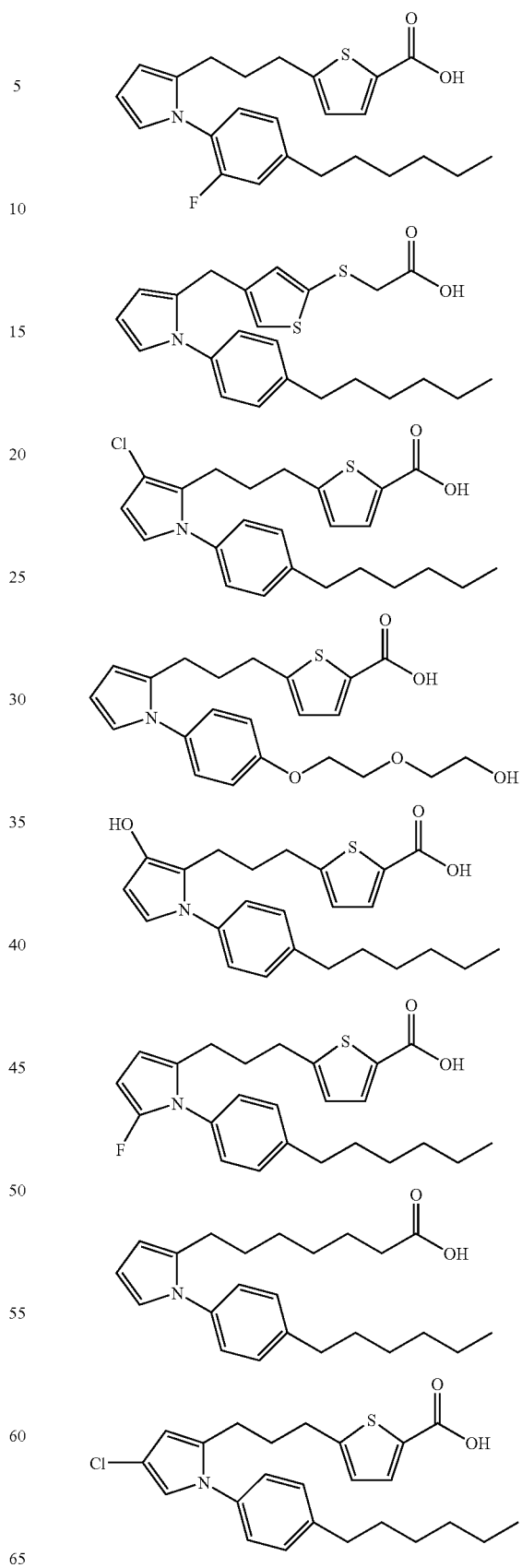

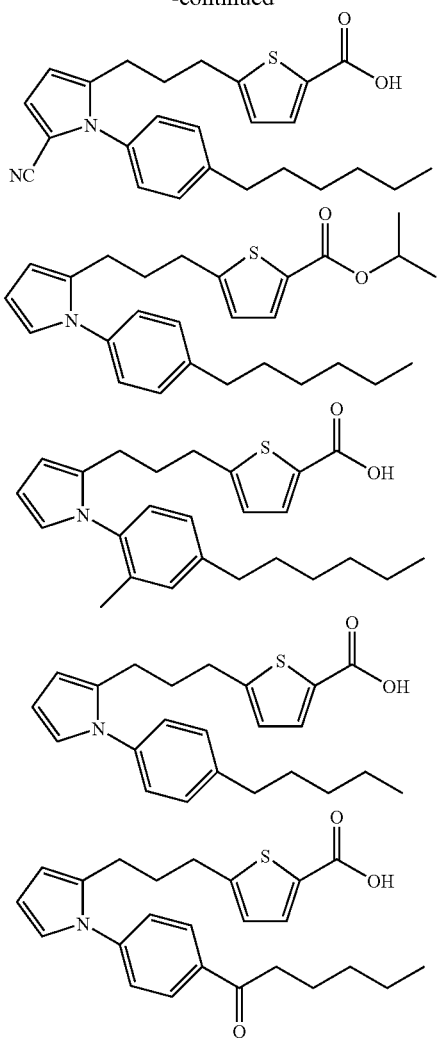
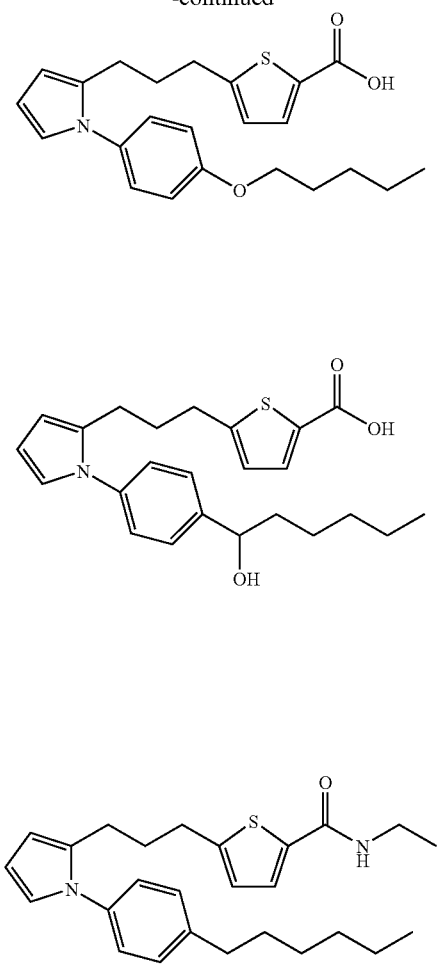
Synthetic Methods
Scheme 1
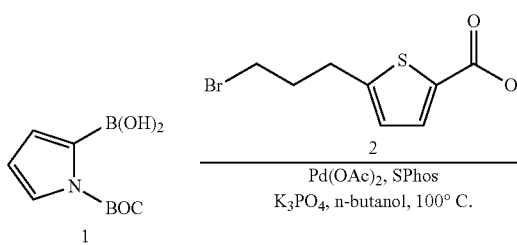
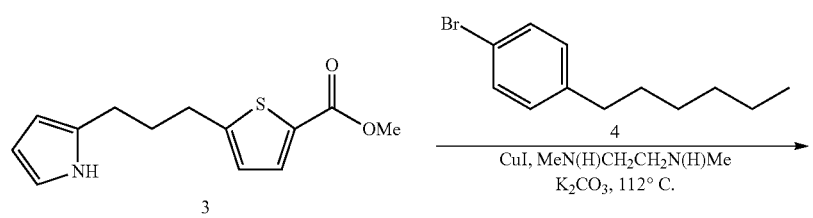

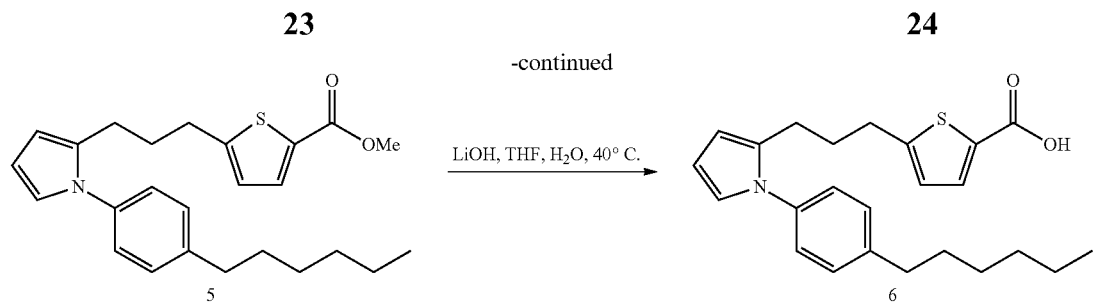

EXAMPLE 1

5-(3-(1-(4-hexylphenyl)-1H-pyrrol-2-yl)propyl)thiophene-2-carboxylic acid (6)

Step 1. Coupling of 1 with 2 to Give 3

Palladium acetate (2.2 mg, 0.01 mmol), 2-dicyclohexylphosphino-2',6'-dimethoxybiphenyl (SPhos, Aldrich Chemical, 12.1 mg, 0.03 mmol), potassium phosphate (212 mg, 1.0 mmol) and 1-BOC-pyrrole-2-boronic acid (1, Combi-Blocks Inc., 158 mg, 0.75 mmol) were combined in a 1-dram vial. Methyl 5-(3-bromopropyl)thiophene-2-carboxylate (2, for example preparation, see WO94/13295, incorporated by reference herein, 132 mg, 0.5 mmol) was added as a solution in n-butanol (Alfa, HPLC grade, 1.0 mL). The reaction mixture was purged with nitrogen, the vial was sealed and placed in a 100° C. oil bath and stirred vigorously. After 18 h, the reaction was allowed to cool to room temperature, diluted with EtOAc and filtered through celite. The filtrate was concentrated in vacuo. Purification of the residue by chromatography on 12 g silica gel using an Isco-Teledyne Combiflash machine (hexanes→20% EtOAc/hexanes, gradient) afforded 22 mg (18%) of 3.

Step 2. Coupling of 3 with 4 to Give 5

Copper (I) iodide (2 mg, 0.011 mmol), pyrrole 3 (11 mg, 0.044 mmol) and potassium carbonate (36 mg, 0.26 mmol) were combined in a 1-dram vial. 1-Bromo-4-n-hexylbenzene (4, Alfa, 0.10 mL, 0.49 mmol) and then N,N'-dimethylethylenediamine (3 L, 0.03 mmol) were added. The reaction mixture was purged with nitrogen, the vial was sealed and placed in a 112° C. oil bath and stirred vigorously. After 24 h, the reaction was allowed to cool to room temperature, diluted with EtOAc and filtered through celite. The filtrate was concentrated in vacuo. Purification of the residue by chromatography on 4 g silica gel using an Isco-Teledyne Combiflash machine (hexanes→20% EtOAc/hexanes, gradient) afforded 8 mg (44%) of 5.

Step 3. Saponification of 5 to Give 6

In a 1-dram vial, ester 5 (8 mg, 0.02 mmol) was dissolved in THF (0.2 mL). Lithium hydroxide (0.1 mL of a 1.0N aqueous solution, 0.1 mmol) was added. The reaction mixture was purged with nitrogen, the vial was sealed and placed in a 40° C. oil bath and stirred vigorously. After 18 h, the reaction was allowed to cool to room temperature, and the solvents were evaporated under a stream of nitrogen. The residue was diluted with water (1 mL) and the mixture was acidified with 1 N HCl (0.5 mL). The mixture was extracted with EtOAc (3×5 mL). The combined organic phase was washed with brine (5 mL), dried ($Na_2SO_4$), filtered and concentrated in vacuo. Purification of the residue by preparative thin layer chromatography (250 M thickness, eluting with EtOAc) afforded 3 mg (39%) of the title compound (6).

This specific example can be readily adapted to obtain a variety of structures using synthetic methods known in the art. For example, compound 2 can be readily replaced with different bromide compounds which may be commercially available or prepared by methods known in the art. Compound 1 and compound 4 may be varied by using compounds with different subtituents on the aromatic ring which may be commercially available or by utilizing electrophilic aromatic substitution methods known in the art, or the aromatic rings may be modified in compound 6 to obtain a variety of compounds. Other synthetic pathways may also be used.

In vitro Testing

US 2007/0129552, incorporated by reference herein, describes the methods used to obtain the in vitro data in the table below.

TABLE 1

| Example | Structure | EP2 data | | | EP4 data | | Other Receptors (EC50 in nM) | | | | | |
| --- | --- | --- | --- | --- | --- | --- | --- | --- | --- | --- | --- | --- |
| | | flipr EC50 | cAMP EC50 | Ki | flipr EC50 | Ki | hFP | hEP1 | hEP3A | hTP | hIP | hDP |
| 1 | | 2820 | 0.7 | 46 | NA | 3984 | NA | NA | NA | NA | NA | 2187 |

What is claimed is:

1. A compound represented by a formula:

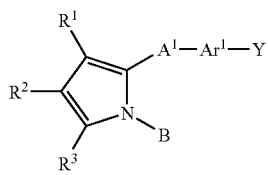

wherein Y is $C_{0-14}H_{1-30}O_{1-4}S_{0-2}N_{0-4}P_{0-1}$ and is: an organic acid functional group, or an amide or ester thereof; hydroxymethyl or an ether thereof; or a tetrazolyl functional group;

$A^1$ is —$(CH_2)_3$—, —$O(CH_2)_2$—, —$S(CH_2)_2$—, —$CH_2OCH_2$—, —$CH_2SCH_2$—, —$(CH_2)_2O$—, or —$(CH_2)_2S$—;

$Ar^1$ is 1,3-attached thienyl, furyl, or pyrrolyl with 0, 1, or 2 substituents selected from, —F, —Cl —Br, —$CH_3$, or —$OCH_3$, $R^1$, $R^2$, and $R^3$ are independently —H, —F, —Cl, —Br, —I, or a moiety of a formula $C_{0-6}H_{0-14}N_{0-1}O_{0-2}S_{0-1}$, B is aryl of a formula $C_{5-20}H_{0-45}N_{0-4}O_{0-4}S_{0-4}F_{0-5}Cl_{0-3}Br_{0-3}I_{0-3}$.

2. The compound of claim 1 wherein Y is —$CO_2R^4$, —$CONR^5R^6$, —$CON(CH_2CH_2OH)_2$, —$CONH(CH_2CH_2OH)$, —$CH_2OH$, —$P(O)(OH)_2$, —$CONHSO_2R^4$, —$SO_2NR^5R^6$,

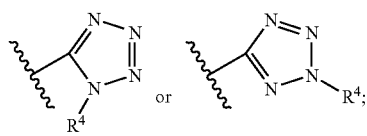

wherein $R^4$, $R^5$ and $R^6$ are independently H, $C_1$-$C_6$ alkyl, $C_{1-6}$ hydroxyalkyl, unsubstituted phenyl, or unsubstituted biphenyl.

3. The compound of claim 1 wherein $R^1$, $R^2$, and $R^3$ are acyclic.

4. The compound of claim 1 wherein $R^1$, $R^2$, and $R^3$ are independently selected from —F, —Cl, —Br, —I, —$CF_3$, —$C(O)CF_3$, —R, —$C(O)R$, —$SO_2NR_2$, —OR, and —$NR_2$, wherein R is independently —H or $C_{1-6}$ alkyl.

5. The compound of claim 1 wherein B is phenyl, pyridinyl, thienyl, or furyl, and B has 1, 2, or 3 substituents independently selected from —F, —Cl, —Br, —I, —$CF_3$, —$C(O)CF_3$, —$R^7$, —$C(O)R^7$, —$SO_2N(R^7)_2$, —$OR^7$, and —$N(R^7)_2$, wherein $R^7$ is $C_{1-10}$ alkyl with 0, 1, 2, or 3 —OH substituents, or $R^7$ is unsubstituted phenyl, pyridinyl, thienyl, or furyl.

6. The compound of claim 1 represented by a formula:

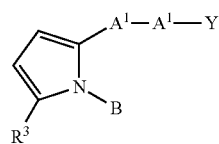

wherein $R^3$ is —H, —F, —Cl, or —Br.

7. The compound of claim 6 wherein B is phenyl with 1 substituent represented by:

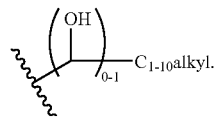

8. The compound of claim 7 wherein Y is —$CO_2R^4$, wherein $R^4$ is —H or $C_{1-6}$ alkyl.

9. The compound of claim 1 represented by a formula:

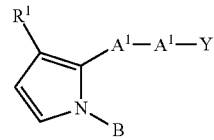

wherein $R^1$ is —H, —F, —Cl, or —Br.

10. The compound of claim 9 wherein B is phenyl with 1 substituent represented by:

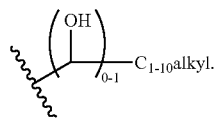

11. The compound of claim 10 wherein Y is —$CO_2R^4$, wherein $R^4$ is —H or $C_{1-6}$ alkyl.

12. The compound of claim 1 represented by a formula:

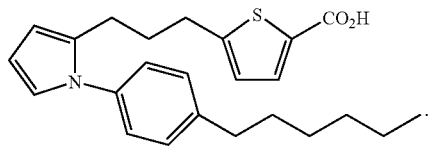

13. The compound of claim 1 wherein Y is:
—$CO_2(CH_2)_2OH$ or

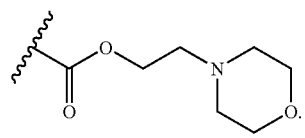

14. The compound of claim 13 represented by a formula:

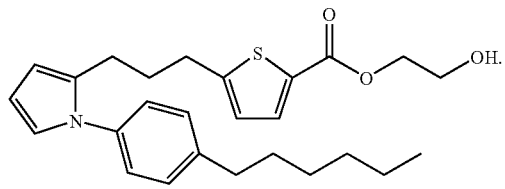

15. A method of: reducing intraocular pressure, growing hair, or improving the appearance of hair, comprising administering a compound according to claim 1 to a mammal in need thereof.

16. The method of claim 15 wherein the compound is:
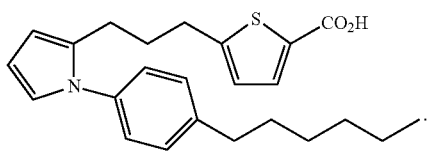
17. The method of claim 15 wherein the mammal is a human being.
18. The method of claim 16 wherein the mammal is a human being.
* * * * *